United States Patent [19]
Riedl et al.

[11] Patent Number: 5,684,023
[45] Date of Patent: Nov. 4, 1997

[54] BENZOFURANYL -AND BENZOTHIENYLOXAZOLIDINONES

[75] Inventors: Bernd Riedl; Dieter Häbich; Andreas Stolle, all of Wuppertal, Germany; Hanno Wild, Orange, Conn.; Rainer Endermann, Wuppertal, Germany; Klaus Dieter Bremm, Recklinghausen, Germany; Hein-Peter Kroll, Wuppertal, Germany; Harald Labischinski, Wuppertal, Germany; Klaus Schaller, Wuppertal, Germany; Hans-Otto Werling, Wuppertal, Germany

[73] Assignee: Bayer Aktiengesellschaft, Leverkusen, Germany

[21] Appl. No.: 503,116

[22] Filed: Jul. 17, 1995

[30] Foreign Application Priority Data

Jul. 20, 1994 [DE] Germany ............... 44 25 609.4

[51] Int. Cl.$^6$ ................................ C07D 413/04
[52] U.S. Cl. ............... 514/337; 514/376; 546/271.4; 548/231
[58] Field of Search ................ 514/376, 337; 548/231, 232; 546/271.4

[56] References Cited

U.S. PATENT DOCUMENTS

| | | | |
|---|---|---|---|
| 4,705,799 | 11/1987 | Gregory | 514/376 |
| 4,801,600 | 1/1989 | Wang et al. | 514/376 |
| 4,921,869 | 5/1990 | Wang et al. | 514/376 |
| 4,965,268 | 10/1990 | Wang et al. | 514/253 |
| 5,182,296 | 1/1993 | Nakai | 514/376 |
| 5,254,577 | 10/1993 | Carlson et al. | 514/376 |
| 5,296,495 | 3/1994 | Matsuo | 514/337 |
| 5,475,014 | 12/1995 | Akasaka | 548/231 |

FOREIGN PATENT DOCUMENTS

| | | |
|---|---|---|
| 0311090 | 4/1989 | European Pat. Off. . |
| 0312000 | 4/1989 | European Pat. Off. . |
| 0693491 | 7/1995 | European Pat. Off. . |
| 4425613 | 1/1996 | Germany . |
| 9002744 | 3/1990 | WIPO . |

OTHER PUBLICATIONS

I.T. Harrison, et al., "Compendium of Organic Synthetic Methods", vol. 1 and 2, Wiley–Interscience, New York, pp. I to XV, and I to SXII respectively only (1971).
C–H. Park, et al., J. Med. Chem., vol. 35, No. 6, pp. 1156–1165, (1992).
Riedl et al. Chem Abstr vol. 124 entry 289520 Abstract EP 693491 (1996).

*Primary Examiner*—Donald G. Daus
*Attorney, Agent, or Firm*—Sprung Kramer Schaefer & Briscoe

[57] ABSTRACT

The present invention relates to benzofuranyl- and benzothienyloxazolidinones, processes for their preparation and their use as medicaments, in particular as antibacterial medicaments.

11 Claims, No Drawings

BENZOFURANYL -AND BENZOTHIENYLOXAZOLIDINONES

The present invention relates to benzofuranyl- and benzothienyloxazolidinones, processes for their preparation and their use as medicaments, in particular as antibacterial medicaments.

The publications U.S. Pat. No. 5,254,577, U.S. Pat. No. 4,705,799, EP 311 090, U.S. Pat. No. 4,801,600, U.S. Pat. No. 4,921,869, U.S. Pat. No. 4,965,268, EP 312 000 and C. H. Park et al., J. Med. Chem. 35, 1156 (1992) disclose N-aryloxazolidinones having antibacterial action.

The present invention relates to benzofuranyl- and benzothienyloxazolidinones of the general formula (I)

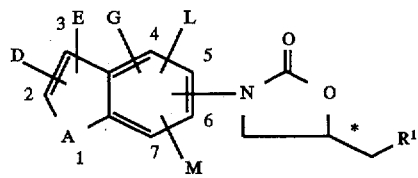

in which
R$^1$ represents azido, hydroxyl or a group of the formula —OR$^2$, —O—SO$_2$R$^3$ or —NR$^4$R$^5$,
wherein
R$^2$ denotes straight-chain or branched acyl having up to 8 carbon atoms or a hydroxyl protective group,
R$^3$ denotes straight-chain or branched alkyl having up to 4 carbon atoms or phenyl which is optionally substituted by a straight-chain or branched alkyl having up to 4 carbon atoms,
R$^4$ and R$^5$ are identical or different and denote cycloalkyl having 3 to 6 carbon atoms, hydrogen, phenyl or straight-chain or branched alkyl having up to 8 carbon atoms or an amino protective group,
or
R$^4$ or R$^5$ denotes a group of the formula —CO—R$^6$,
wherein
R$^6$ denotes cycloalkyl having 3 to 6 carbon atoms, straight-chain or branched alkyl or alkoxy in each case having up to 8 carbon atoms, phenyl or hydrogen,
A represents an oxygen or sulphur atom,
D, E, G, L and M are identical or different and represent hydrogen, carboxyl, halogen, cyano, mercapto, formyl, trifluoromethyl, nitro, straight-chain or branched alkoxy, alkoxycarbonyl, alkylthio, or acyl in each case having up to 6 carbon atoms, or straight-chain or branched alkyl having up to 6 carbon atoms, which for its part can be substituted by hydroxyl, by straight-chain or branched alkoxy or acyl having up to 5 carbon atoms or by a radical of the formula

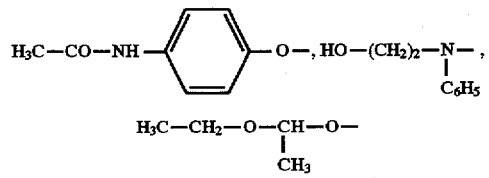

of by a group of the formula —NR$^7$R$^8$,
wherein
R$^7$ and R$^8$ are identical or different and denote hydrogen, straight-chain or branched alkyl having up to 4 carbon atoms or phenyl, or together with the nitrogen atom form a 5- to 6-membered, saturated heterocycle optionally containing a further heteroatom from the series N, S and/or O, which for its part can optionally also be substituted on a further nitrogen atom by straight-chain or branched alkyl or acyl having up to 3 carbon atoms,
and/or
optionally represent a group of the formula —NR$^{7'}$R$^{8'}$,
wherein
R$^{7'}$ and R$^{8'}$ are identical or different and have the meaning of R$^7$ and R$^8$ indicated above and are identical to or different from this,
and/or
optionally represent (C$_2$-C$_8$)-alkenylphenyl, phenyl or a 5- or 6-membered saturated or unsaturated heterocycle having up to 3 heteroatoms from the series S, N and/or O, which for their part are optionally substituted by a group of the formula —CO—NR$^9$R$^{10}$, —NR$^{11}$R$^{12}$—NR$^{13}$—SO$_2$—R$^{14}$, —R$^{15}$R$^{16}$N—SO$_2$— or —R$^{17}$—S(O)$_a$—,
wherein
a denotes a number 0, 1 or 2,
R$^9$, R$^{10}$, R$^{13}$, R$^{15}$ and R$^{16}$ are identical or different and denote hydrogen, straight-chain or branched alkyl having up to 6 carbon atoms or phenyl,
R$^{11}$ and R$^{12}$ are identical or different and have the meaning of R$^7$ and R$^8$ indicated above and are identical to or different from this,
R$^{14}$ and R$^{17}$ are identical or different and have the meaning of R$^3$ indicated abound are identical to or different from this, and/or for their part are optionally substituted up to 2 times by identical or different substituents from the series consisting of carboxyl, halogen, cyano, mercapto, formyl, trifluoromethyl, nitro, phenyl, straight-chain or branched alkoxy, alkoxycarbonyl, alkylthio and acyl in each case having up to 6 carbon atoms or straight-chain or branched alkyl having up to 6 carbon atoms, which for its part can be substituted by hydroxyl, by straight-chain or branched alkoxy or acyl having up to 5 carbon atoms or by a group of the formula —NR$^{18}$R$^{19}$,
wherein
R$^{18}$ and R$^{19}$ have the meaning of R$^7$ and R$^8$ indicated above and are identical to or different from this,
and their salts and S-oxides.

Physiologically acceptable salts of the benzofuranyl- and benzothienyloxazolidinones can be salts of the substances according to the invention with mineral acids, carboxylic acids or sulphonic acids. Particularly preferred salts are e.g. those with hydrochloric acid, hydrobromic acid, sulphuric acid, phosphoric acid, methanesulphonic acid, ethanesulphonic acid, toluenesulphonic acid, benzene sulphonic acid, naphthalene disulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

The compounds according to the invention can exist in stereoisomeric forms which either behave as image and minor image (enantiomers), or which do not behave as image and mirror image (diastereomers). The invention relates both to the enantiomers and diastereomers or their respective mixtures. Like the diastereomers, the racemic forms can also be separated into the stereoisomerically uniform constituents in a known manner.

Heterocycle in general represents a 5- to 6-membered, saturated or unsaturated ring which as heteroatoms can contain up to 3 oxygen, sulphur and/or nitrogen atoms. The following are mentioned as preferred: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

These also include N-bonded, 5- to 6-membered saturated heterocycles which additionally can contain up to 2 oxygen, sulphur and/or nitrogen atoms as heteroatoms, such as, for example, piperidyl, morpholinyl or piperazinyl or pyrrolidinyl. Piperidyl and pyrrolidinyl are particularly preferred.

Hydroxyl protective group in the context of the definition indicated above in general represents a protective group from the series: trimethylsilyl, triisopropylsilyl, tert-butyl-dimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Acetyl, tert-butyldimethylsilyl and tetrahydropyranyl are preferred.

Amino protective groups in the context of the invention are the customary amino protective groups used in peptide chemistry.

These preferably include: benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl.

Preferred compounds of the general formula (I) are those in which $R^1$ represents azido, hydroxyl or a group of the formula —$OR^2$, —$OSO_2R^3$ or —$NR^4R^5$,
wherein $R^2$ denotes straight-chain or branched acyl having up to 6 carbon atoms or benzyl, $R^3$ denotes straight-chain or branched alkyl having up to 3 carbon atoms, phenyl or toluoyl, $R^4$ and $R^5$ are identical or different and denote cyclopropyl, cyclopentyl, cyclohexyl, hydrogen, phenyl or straight-chain or branched alkyl or alkoxy in each case having up to 6 carbon atoms, tert-butoxycarbonyl or benzyloxycarbonyl, or $R^4$ or $R^5$ denotes a group of the formula —CO—$R^6$,
wherein $R^6$ denotes cyclopropyl, cyclobutyl, cyclopentyl, cyclohexyl or straight-chain or branched alkyl or alkoxy in each case having up to 6 carbon atoms, phenyl or hydrogen, A represents an oxygen or sulphur atom, D, E, G, L and M are identical or different and represent hydrogen, carboxyl, fluorine, chlorine, bromine, iodine, cyano, mercapto, trifluoromethyl, formyl, nitro, straight-chain or branched alkoxy, alkoxycarbonyl, alkylthio or acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms, by a radical of the formula

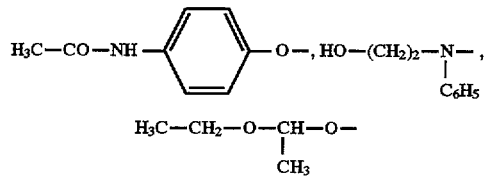

or by a group of the formula —$NR^7R^8$,
wherein $R^7$ and $R^8$ are identical or different and denote hydrogen, straight-chain or branched alkyl having up to 3 carbon atoms or phenyl, or together with the nitrogen atom form a morpholinyl, pyrrolidinyl, piperazinyl or piperidyl ring, each of which is optionally substituted, also via the free N function, by methyl, ethyl or acetyl,
and/or optionally represent a group of the formula —$NR^{7'}R^{8'}$,
wherein $R^{7'}$ and $R^{8'}$ have the meaning of $R^7$ and $R^8$ indicated above and are identical to or different from this,
and/or optionally represent ($C_2$-$C_4$)-alkenylphenyl, phenyl, pyridyl or thienyl, which for their parts are optionally substituted by a group of the formula —CO—$NR^9R^{10}$, —$NR^{11}R^{12}$, —$NR^{13}$—$SO_2$—$R^{14}$, —$R^{15}R^{16}N$—$SO_2$— or —$R^{17}$—$S(O)_a$—,
wherein a denotes a number 0, 1 or 2, $R^9$, $R^{10}$, $R^{13}$, $R^{15}$ and $R^{16}$ are identical or different and denote hydrogen, straight-chain or branched alkyl having up to 4 carbon atoms or phenyl, $R^{11}$ and $R^{12}$ are identical or different and have the meaning of $R^7$ and $R^8$ indicated above and are identical to or different from this, $R^{14}$ and $R^{17}$ are identical or different and have the meaning of $R^3$ indicated above and are identical to or different from this, and/or for their part are optionally substituted up to 2 times by identical or different substituents from the series consisting of carboxyl, fluorine, chlorine, bromine, iodine, cyano, mercapto, trifluoromethyl, formyl, nitro, phenyl, straight-chain or branched alkoxy, alkoxycarbonyl, alkylthio and acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms or by a group of the formula —$NR^{18}R^{19}$,
wherein $R^{18}$ and $R^{19}$ have the meaning of $R^7$ and $R^8$ indicated above and are identical to or different from this, and their salts and S-oxides.

Particularly preferred compounds of the general formula (I) are those in which $R^1$ represents azido, hydroxyl or a group of the formula $-OR^2$, $-OSO_2R^3$ or $-NR^4R^5$, wherein $R^2$ denotes a straight-chain or branched acyl having up to 6 carbon atoms, $R^3$ denotes methyl, ethyl, phenyl or toluoyl, $R^4$ and $R^5$ are identical or different and denote cyclopropyl, cyclopentyl, cyclohexyl, hydrogen, phenyl or straight-chain or branched alkyl having up to 5 carbon atoms, or $R^4$ or $R^5$ denotes a group of the formula $-CO-R^6$, wherein $R^6$ denotes cyclopropyl, cyclopentyl, cyclohexyl or straight-chain or branched alkyl or alkoxy in each case having up to 4 carbon atoms, hydrogen or phenyl, -

A represents an oxygen or sulphur atom,

D, E, G, L and M are identical or different and represent hydrogen, carboxyl, fluorine, chlorine, bromine, iodine, cyano, formyl, trifluoromethyl, nitro, straight-chain or branched alkoxy, alkoxycarbonyl or acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms, by a radical of the formula

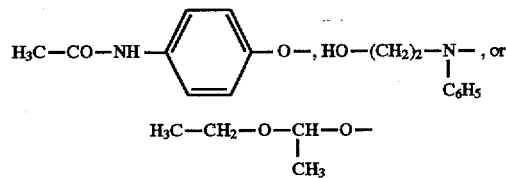

or by a group of the formula $-NR^7R^8$, wherein $R^7$ and $R^8$ are identical or different and denote hydrogen or methyl, or together with the nitrogen atom form a morpholinyl, pyrrolidinyl, piperazinyl or piperidyl ring, each of which is optionally substituted, also via the free N function, by methyl, ethyl or acetyl, and/or optionally represent a group of the formula $-NR^{7'}R^{8'}$, wherein $R^{7'}$ and $R^{8'}$ have the meaning of $R^7$ and $R^8$ indicated above and are identical to or different from this, and/or optionally represent 2-phenylvinyl, phenyl, pyridyl or thienyl, which for their parts are optionally substituted by a group of the formula $-CO-NR^9R^{10}$ or $-NR^{11}R^{12}$, wherein $R^9$ and $R^{10}$ are identical or different and denote hydrogen or methyl, $R^{11}$ and $R^{12}$ are identical or different and have the meaning of $R^7$ and $R^8$ indicated above and are identical to or different from this, and/or for their part are optionally substituted up to 2 times by identical or different substituents from the series consisting of carboxyl, fluorine, chlorine, bromine, iodine, cyano, formyl, trifluoromethyl, nitro, phenyl, straight-chain or branched alkoxy, alkoxycarbonyl and acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms or by a group of the formula $-NR^{18}R^{19}$, wherein $R^{18}$ and $R^{19}$ have the meaning of $R^7$ and $R^8$ indicated above and are identical to or different from this, and their salts and S-oxides.

Very particularly preferred compounds of the general formula (I) are those in which G, L and M represent hydrogen and the oxazolidinone radical is bonded to the phenyl ring in position 5 or 6.

Processes for the preparation of the compounds of the general formula (I) according to the invention have additionally been found, characterized in that

[A] compounds of the general formula (II) or (III)

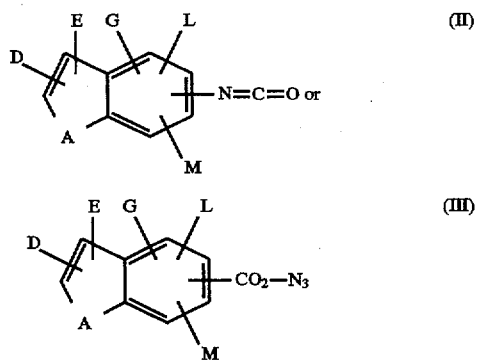

in which

A, D, E, G, L and M have the meanings indicated above, are reacted with lithium bromide/$(C_4H_9)_3P(O)$ and epoxides of the general formula (IV)

in which

T represents $C_1$–$C_6$-acyloxy, in inert solvents, if appropriate in the presence of a base, and if $R^1$=OH the hydroxyl function is liberated by a typical ester hydrolysis or by a typical transesterification, or

[B] compounds of the general formula (V)

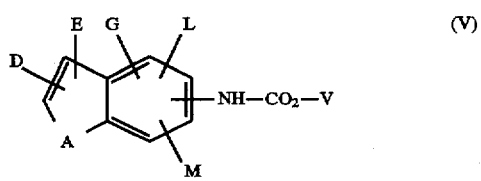

in which

A, D, E, G, L and M have the meaning indicated above and

V represents a typical protective group, preferably benzyl, are reacted in inert solvents and in the presence of a base, for example lithium alkyls or lithium-N-alkyl- or lithium-N-silylalkylamides, preferably N-butyllithium, with epoxides of the general formula (IV), or

[C] if $R^1$—OH, first compounds of the general formula (III) are converted by elimination of nitrogen in alcohol to the compounds of the general formula (Va)

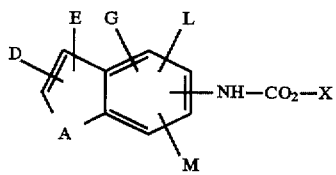

(Va)

in which

A, D, E, G, L and M have the meaning indicated above and

X represents straight-chain or branched $C_2$-$C_6$-alkyl, preferably n-butyl, and in a second step reacted as described under [A] in inert solvents and in the presence of a base, preferably lithium-N-alkyl- or N-silylalkylamides or n-butyllithium and epoxides of the general formula (IV), or

[D] compounds of the general formula (VI)

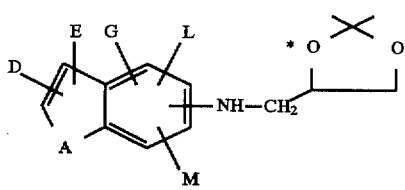

(VI)

in which

A, D, E, G, L and M have the meaning indicated above, are either reacted directly with acids and diethyl carbonate, or first by reaction of the compounds of the general formula (VI) with acids, the compounds of the general formula (VII)

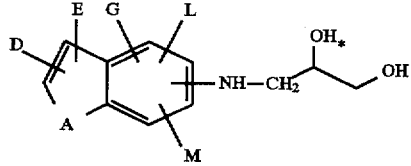

(VII)

in which

A, D, E, G, L and M have the meaning indicated above, are prepared, and then cyclized in inert solvents in the presence of an auxiliary, or

[E] fast compounds of the general formula (Ia)

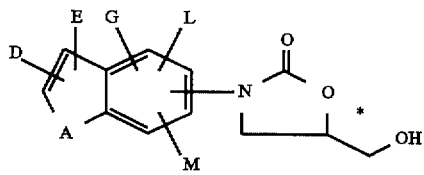

(Ia)

in which

A, D, E, G, L and M have the meaning indicated above, are converted by reaction with ($C_1$-$C_4$)-alkyl- or phenyl-sulfonyl chlorides in inert solvents and in the presence of a base to the corresponding compounds of the general formula (Ib)

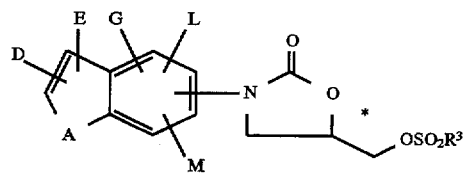

(Ib)

in which

A, D, E, G, L, M and $R^3$ have the meaning indicated above, then, with sodium azide in inert solvents, the azides of the general formula (Ic)

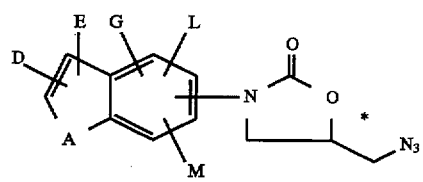

(Ic)

in which

A, D, E, G, L and M have the meaning indicated above, are prepared, in a further step the products are converted by reaction with ($C_1$-$C_4$—O)$_3$—P or $Ph_3P$, preferably ($CH_3O)_3P$, in inert solvents and with acids to the amines of the general formula (Id)

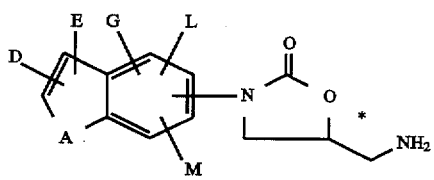

(Id)

in which

A, D, E, G, L and M have the meaning indicated above, and by reaction with acetic anhydride or other acylating agents of the general formula (VIII)

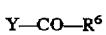

Y—CO—$R^6$ (VIII)

in which $R^6$ has the meaning indicated above and

Y represents halogen, preferably chlorine or the radical —OCOR$^6$, in inert solvents the compounds of the general formula (Ie)

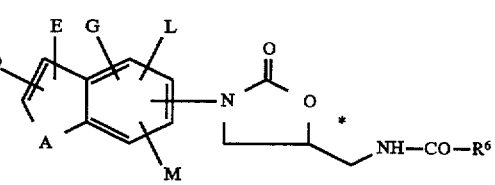

(Ie)

in which

A, D, E, G, L, M and $R^6$ have the meaning indicated above, are prepared, or

[F] compounds of the general formula (Ie) are converted by a halogenation, if appropriate in the presence of a silver catalyst, to the compounds of the general formula (If)

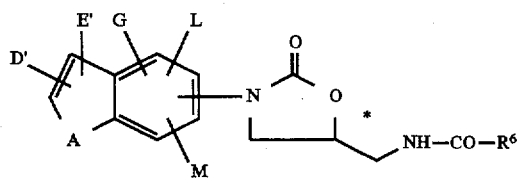

in which

D' or E' represents halogen, preferably bromine or iodine, and

A, G, L, M and $R^6$ have the meaning indicated above, or

[G] compounds of the general formula (If) are reacted with compounds of the general formula (IX)

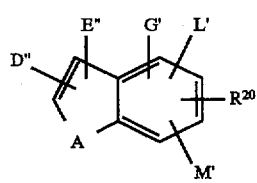

in which

A has the meaning indicated above and

D", E", G', L' and/or M' represent one of the optionally substituted, monocyclic heterocycles mentioned above under D, E, G, L and M, phenyl or $(C_2-C_8)$-alkenylphenyl, and $R^{20}$ represents the boronic acid radical $-B(OH)_2$ or represents an organotin radical of the formula $-SnR^{21}R^{22}R^{23}$, wherein $R^{21}$, $R^{22}$ and $R^{23}$ are identical or different and denote $C_1-C_4$-alkyl, in inert solvents and in the presence of a palladium catalyst, or

[H] if A=O compounds of the formula (X)

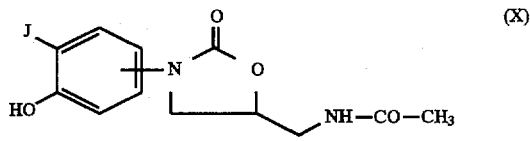

are cyclized by reaction with propargyl alcohol in inert solvents and in the system $Pd(P(C_6H_5)_3)_2(OAc)_2/CuI$, NaOAc, and in the case of the S-oxides an oxidation is carried out, and if $R^4$, $R^5$, $R^9$, $R^{10}$, $R^{11}$, $R^{12}$, $R^{13}$, $R^{15}$, $R^{16}$, $R^{18}$ and $R^{19} \neq H$ an alkylation is carried out by customary methods, and if appropriate further substituents or functional groups which are already present are introduced or derivatized by customary methods, such as, for example, redox reactions, substitution reactions and/or hydrolysis or incorporation and decomposition of protective groups.

The processes according to the invention can be illustrated by way of example by the following reaction schemes:

[A]

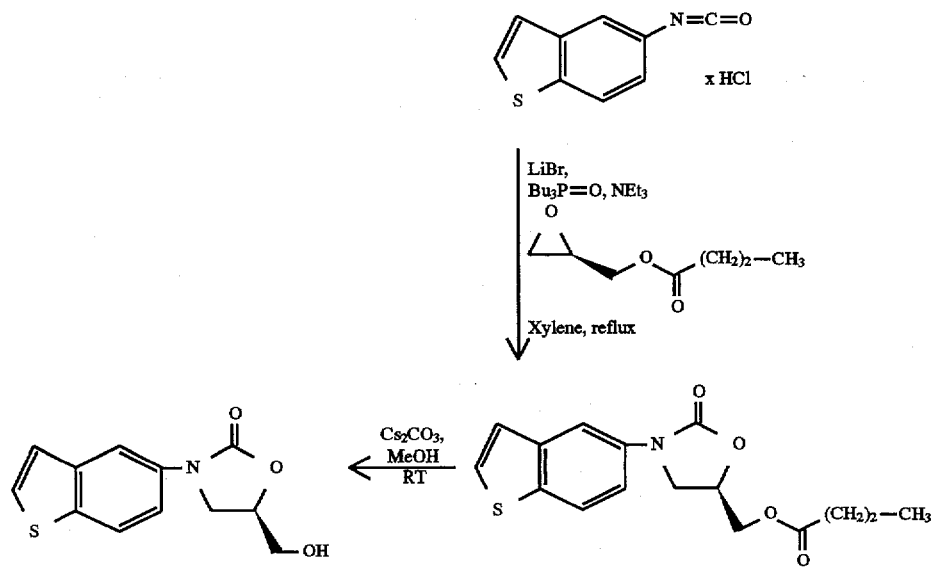

[A]

-continued
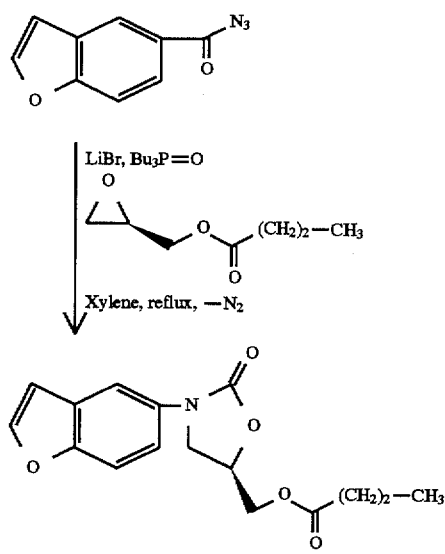
[B]
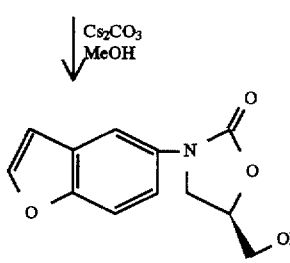
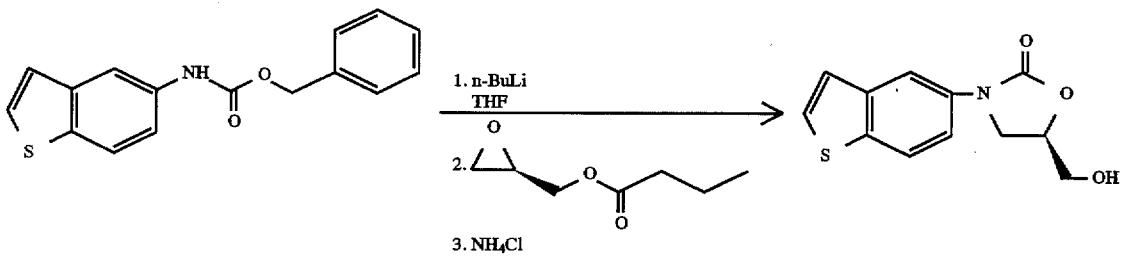
[C]
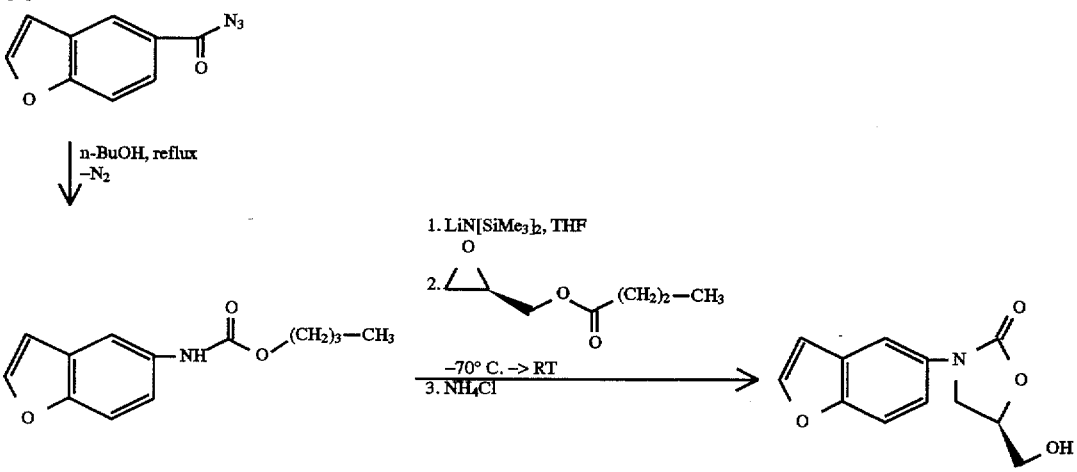
[D]

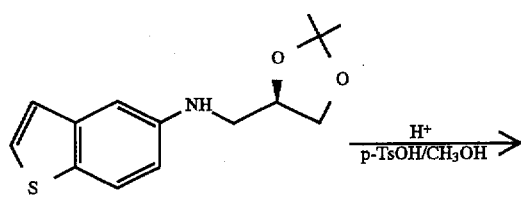
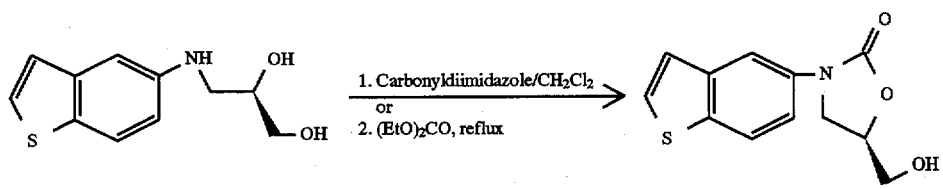
[E]
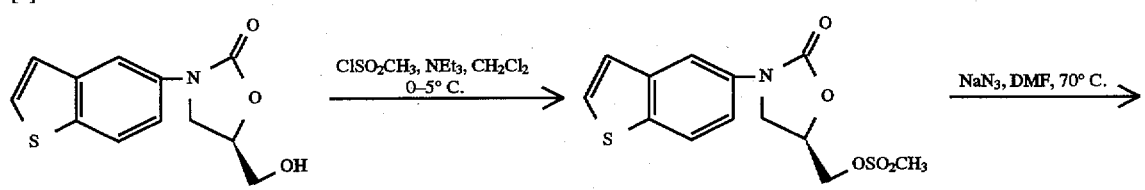
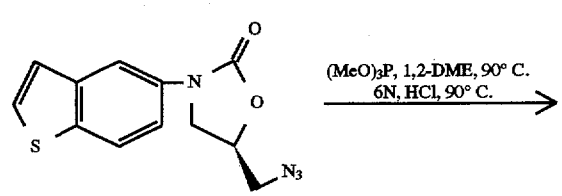
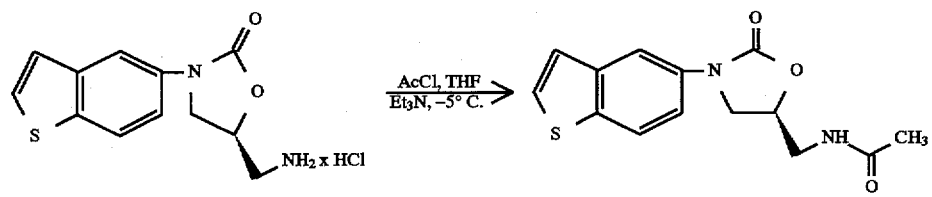
[F]
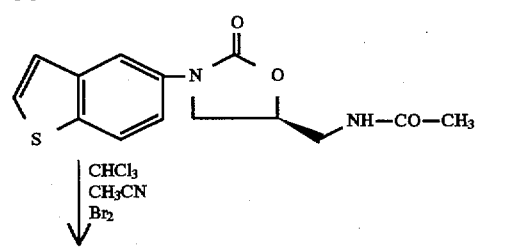
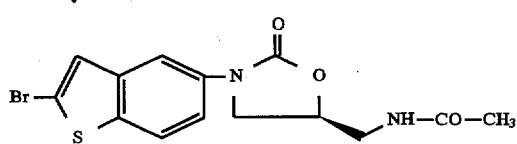
[G]

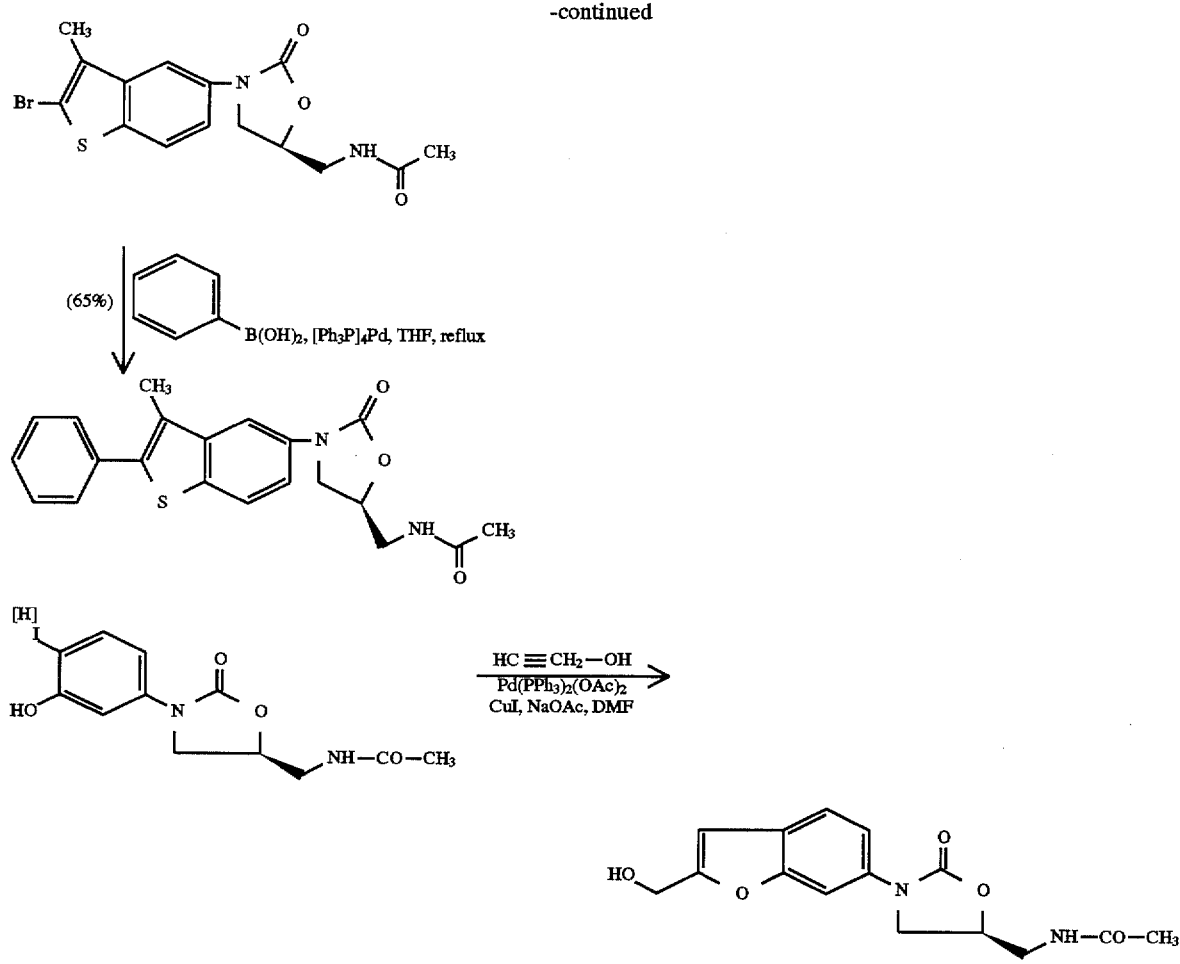

Depending on the individual process steps, suitable solvents are the customary solvents which do not change under the reaction conditions. The preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethyl formamide or hexamethylphosphoramide, or hydrocarbons such as hexane, benzene, dichlorobenzene, xylene or toluene, or dimethyl sulphoxide, acetonitrile, ethyl acetate or halogenohydrocarbon such as methylene chloride, chloroform or carbon tetrachloride, or pyridine, picoline or N-methylpiperidine. Mixtures of the solvents mentioned can also be used.

Depending on the individual process steps, suitable bases are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyldiisopropylamine, triethylamine, picoline, pyridine or N-methylpiperidine, or amides such as sodium amide or lithium diisopropylamide, or lithium N-silylalkylamides, such as, for example, lithium N-(bis) triphenylsilylamide or lithium alkyls such as n-butyllithium.

The base is employed in an amount from 1 mol to 10 mol, preferably from 1 mol to 3 mol, relative to 1 mol of the compounds of the general formulae (II), (III), (IV) and (Va).

All reactions are in general carried out at normal, elevated or reduced pressure (e.g. 0.5 to 5 bar). In general the reactions are carried out at normal pressure.

Process [A] is preferably carried out in xylene or dichlorobenzene, if appropriate in the presence of triethylamine under reflux.

The base-catalysed transesterification is carried out using one of the abovementioned alcohols, preferably methanol, in a temperature range from −10° C. to +40° C., preferably at room temperature.

Suitable bases are in general sodium hydrogen carbonate, sodium methoxide, hydrazine hydrate, potassium carbonate or caesium carbonate. Caesium carbonate is preferred.

Process [B] is carried out in one of the abovementioned ethers using lithium alkyl compounds or lithium N-silylamides, such as, for example n-butyllithium, lithium diisopropylamide or lithium bis-trimethylsilylamide, preferably in tetrahydrofuran and lithium bis-trimethylsilylamide or n-butyllithium, in a temperature range from −100° C. to +20° C., preferably from −75° C. to −40° C.

For process [C], suitable alcohols for the 1st step are preferably those mentioned above, in the case of subsequent cyclization tetrahydrofuran.

Suitable bases for the cyclization are preferably the abovementioned lithium N-silylalkyl compounds or n-butyllithium. n-Butyllithium is particularly preferred.

The first reaction step is carried out at the boiling point of the corresponding alcohol and the cyclisation in a temperature range from −70° C. to room temperature.

The cyclisation [D] is carried out in the presence of an auxiliary and/or in the presence of an acid.

Suitable acids are in general inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids containing $C_1$–$C_4$-alkyl radicals or aryl radicals, such as, for example, methanesulphonic acid, ethanesulphonic acid, benzenesulphonic acid or toluenesulphonic acid. Hydrochloric acid is particularly preferred.

The acid is employed in an amount from 1 mol to 10 mol, preferably from 1 mol to 2 mol, based on 1 mol of the compounds of the general formula (VI).

Suitable auxiliaries are the customary reagents such as phosgene, carbonyldiimidazole, or diethyl carbonate or trichloromethyl chloroformate. Carbonyldiimidazole, diethyl carbonate or trichloromethyl chloroformate is preferred.

Suitable solvents are the abovementioned halogenohydrocarbons. Methylene chloride is preferred.

The cyclisations are in general carried out in a temperature range from –20° C. to 100° C., preferably at –20° C. to room temperature.

The acylation [E] is in general carried out in one of the abovementioned ethers or halogenohydrocarbons, preferably tetrahydrofuran or methylene chloride, in a temperature range from –30° C. to 50° C., preferably from –10° C. to room temperature.

The coupling reaction [G] with the boronic acid and aryl tin compounds is likewise carried out in one of the abovementioned ethers or hydrocarbons, preferably tetrahydrofuran or toluene, and in the presence of a palladium complex.

Suitable palladium complexes are, for example, Pd[P$(C_6H_5)_3]_4$, $[(C_6H_5)_3P]_2PdCl_2$ or $(C_6H_5CN)_2PdCl_2$. $[(C_6H_5)_3P]_4Pd$ is preferred.

The reaction is carried out in a temperature range from room temperature to 150° C., preferably at the boiling point of the respective solvent.

The reductions are in general carried out using hydrides in inert solvents or using boranes, diboranes or their complex compounds.

Preferably, the reductions are carried out using hydrides, such as complex borohydrides or aluminium hydrides and also boranes. Sodium borohydride, lithium borohydride, sodium cyanoborohydride, lithium aluminium hydride, sodium bis-(2-methoxyethoxy)-aluminium hydride or borane-tetrahydrofuran are particularly preferably employed in this case.

The reduction is in general carried out in a temperature range from –50° C. up to the respective boiling point of the solvent, preferably from –20° C. to +90° C.

The reductions can in general be carried out by hydrogen in water or in inert organic solvents such as alcohols, ethers or halogenohydrocarbon, or their mixtures, using catalysts such as Raney nickel, palladium, palladium on animal carbon or platinum, or using hydrides or boranes in inert solvents, if appropriate in the presence of a catalyst.

The reaction is preferably carried out using hydrides, such as complex borohydrides or aluminium hydrides. Sodium borohydride, lithium aluminium hydride or sodium cyanoborohydride are particularly preferably employed in this case.

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether or amides such as hexamethylphosphoramide or dimethylformamide, or acetic acid. It is also possible to use mixtures of the solvents mentioned.

The oxidation to the N-oxide is in general carried out in one of the abovementioned solvents, preferably in methylene chloride, using oxidizing agents such as, for example, metachloroperbenzoic acid, hydrogen peroxide or peracetic acid, preferably using metachloroperbenzoic acid in a temperature range from 0° C. to 80° C., preferably from 0° C. to 40° C.

The removal of the hydroxyl protective groups is in general carried out according to a customary method, for example by hydrogenolytic cleavage of the benzyl ethers in the abovementioned inert solvents in the presence of a catalyst using hydrogen gas.

The amino protective group is in general likewise removed by customary methods, to be specific preferably Boc using hydrochloric acid in dioxane, Fmoc using piperidine and Z using HBr/HOAc or by hydrogenolysis.

The abovementioned other derivatization reactions are in general carried out according to the methods published in Compendium of Organic Synthetic Methods, T. T. Harrison and S. Harrison, Wiley Interscience.

Redox reactions, reductive amination, transesterification and the halogenation of methyl groups using N-bromosuccinimide (NBS) or N-chlorosuccinimide (NCS) are preferably mentioned, which are illustrated by way of example in the following.

Suitable solvents for the alkylation are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Dichloromethane, dimethyl sulphoxide and dimethylformamide are preferred.

The alkylation is carried out at normal pressure in the abovementioned solvents at temperatures from 0° C. to +150° C., preferably at room temperature to +100° C.

The amidation and the sulphoamidation are in general carried out in inert solvents in the presence of a base and of a dehydrating agent.

Suitable solvents in this case are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane or petroleum fractions, nitromethane, dimethylformamide, acetonitrile or tetrahydrofuran. It is also possible to employ mixtures of the solvents. Dichloromethane and tetrahydrofuran and particularly preferred.

Suitable bases for the amidation and the sulphoamidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate or potassium carbonate, or alkali metal alkoxides such as, for example, sodium methoxide or ethoxide, potassium methoxide or ethoxide or potassium tert-butoxide, or organic amines such as benzyltrimethylammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out at normal pressure. However, it is also possible to carry out the process at reduced pressure or at elevated pressure (e.g. in a range from 0.5 to 5 bar).

When carrying out the amidation and the sulphoamidation, the base is in general employed in an amount from 1 to 3 mol, preferably from 1 to 1.5 mol, relative to 1 mol of the respective carboxylic acid.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or 4-dimethylaminopyridine.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethyl formamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis the base is in general employed in an amount from 1 to 3 mol, preferably from 1 to 1.5 mol, relative to 1 mol of the ester. Molar mounts of the reactants are particularly preferably used.

The esterification is in general carried out using the appropriate alcohols in the presence of acids, preferably sulphuric acid, in a temperature range from 0° C. to 150° C., preferably from 50° C. to 100° C., and at normal pressure.

The compounds of the general formulae (IV), (VIII) and (IX) are known or can be prepared by customary methods.

The compounds of the general formula (VII) are in the main new and can be prepared, for example, as described above.

The compounds of the general formula (II) are known in some cases or are new and can then be prepared, for example, by reacting the appropriate amines with trichloroethyl chloroformates in one of the abovementioned solvents, preferably xylene, at reflux temperature.

The compounds of the general formula (III) are known in some cases or are new and can then be prepared, for example, starting from the appropriate carboxylic acids, by reacting either with isobutyl chloroformate/acetone, sodium azide/water or with diphenylphosphoryl azide/tetrahydrofuran or with xylene or methylene chloride in the presence of one of the bases indicated above, preferably triethylamine, at −10° C. to room temperature.

The compounds of the general formulae (V) and (Va) are known in some cases or are new and can be prepared either by removal of nitrogen from the corresponding carboxylic acid azides and reaction with the appropriate alcohols or by reaction of the corresponding amines with chloroformic acid esters, preferably benzyl chloroformate, in one of the abovementioned solvents, preferably tetrahydrofuran or dioxane, in a temperature range from −10° C. to 200° C., preferably from 0° C. to 150° C.

The compounds of the general formula (VII) are in the main new and can be prepared as described above.

The compounds of the general formula (Ia) are new and can be prepared, for example, as described under [A], [B], [D] or [E].

The compounds of the general formulae (Ib), (Ic), (Id), (Ie) and (If) are new and can be prepared as described above.

The compounds of the general formula (VI) are in the main known or are new and can be prepared, for example, starting from the free amines (Ia), by reacting either with the acetonide of glyceraldehyde in methanol and in the presence of sodium acetate/sodium cyanoborohydride or of sodium borohydride and methanol in a temperature range from −20° C. to +40° C., preferably from −10° C. to 20° C., and at normal pressure.

The introduction of the halogen atom Y (compounds of the general formula (If)) is carried out in the case of bromine and iodine either using elemental bromine or iodine, or in the case of bromine or iodine in the presence of a silver salt, in one of the abovementioned solvents, preferably methylene chloride, acetonitrile or chloroform, in a temperature range from −30° C. to +60° C., preferably from 0° C. to +30° C., and at normal pressure.

Suitable silver salts are, for example, silver tetrafluoroborate, silver trifluoromethanesulphonate or silver trifluoroacetate.

The compound of the formula (X) is covered by the scope of meaning of the publication, but as a species is new and can be prepared, starting from the known 3-methoxy-substituted phenyl-2-oxazolidinone, by carrying out an iodination with $I_2$ in the presence of Ag(OAc) in acetonitrile and chloroform and then liberating the hydroxyl function using $BBr_3$ in dichloromethane.

Process [H] is carried out in one of the abovementioned solvents, preferably dimethylformamide, in a temperature range from 40° C. to 80° C., preferably 60° C., and at normal pressure.

The minimum inhibitory concentrations (MIC) were determined by serial dilution methods on Iso-Sensitest agar (Oxoid). For each test substance, a number of agar plates were prepared which contained a decreasing concentration of the active compound on double dilution in each case. The agar plates were inoculated with a multipoint inoculator (Denley). For inoculation, overnight cultures of the bacilli were used which were previously diluted such that each inoculation point contained about $10^4$ colony-forming particles. The inoculated agar plates were incubated at 37° C., and the bacterial growth was read off after about 20 hours.

The MIC value (μg/ml) indicates the lowest active compound concentration at which no growth could be detected using the naked eye.

The MIC values were determined in BH medium with the aid of the microdilution method. Each test substance was dissolved in the nutrient medium. A concentration series of the test substances was prepared in the microtiter plates by serial dilution. For inoculation, overnight cultures of the bacilli were used which had previously been diluted 1:250 in the nutrient medium. 100 μl each of inoculation solution were added to 100 μl of the diluted, active compound-containing nutrient solutions. The microtiter plates were incubated at 37° C. and read off after about 20 hours. The MIC value (μg/ml) indicates the lowest active compound concentration at which no growth could be detected.

| | MIC values (μg/ml): | | | | | | |
|---|---|---|---|---|---|---|---|
| Ex. No. | Staph. 133 | Staph. 48N | Staph 25701 | Staph 9TV | E. coli Neumann | Klebs. 57 USA | Psdm. Bonn |
| 9 | 4 | 4 | 2 | 2 | >64 | >64 | >64 |
| 16 | 1 | 1 | 1 | 0.5 | >64 | >64 | >64 |
| 27 | 16 | 16 | 16 | 8 | >64 | >64 | >64 |

Compounds of the general formulae (I), (Ia), (Ib), (Ic), (Id), (Ie) and (If) according to the invention have a broad antibacterial spectrum combined with low toxicity, especially against gram-positive bacteria as well as mycobacteria, corynebacteria, Haemophilus influenzae and anaerobic micro-organisms. These properties make possible their use as chemotherapeutic active compounds in human and veterinary medicine.

The compounds according to the invention are active against a broad spectrum of micro-organisms. With their aid, gram-positive bacteria and bacteria-like micro-organisms, such as mycoplasma, can be controlled and the diseases produced by these pathogens can be prevented, ameliorated and/or cured.

The compounds according to the invention are particularly active against bacteria and bacteria-like micro-organisms. They are therefore particularly well suited for the prophylaxis and chemotherapy of local and systemic infections in human and veterinary medicine which are caused by such pathogens.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound or compounds can optionally also be present in one or more of the excipients indicated above in micro-encapsulated form.

The therapeutically active compounds should be present in the abovementioned pharmaceutical preparations in a concentration of about 0.1 to 99.5, preferably of about 0.5 to 95, % by weight of the total mixture.

In addition to the compounds according to the invention, the abovementioned pharmaceutical preparations can also contain further pharmaceutical active compounds.

In general, it has proven advantageous both in human and in veterinary medicine to administer the active compound or compounds according to the invention in total amounts of about 0.5 to 500, preferably 5 to 100, mg/kg of body weight every 24 hours, if appropriate in the form of several individual doses, to achieve the desired results. An individual dose contains the active compound or compounds according to the invention preferably in mounts from about 1 to 80, in particular 3 to 30, mg/kg of body weight.

The new compounds can be combined in the customary concentrations and preparations together with the feed or lactamase inhibitors, e.g. with penicillins which are particularly resistant to penicillinase and clavulanic acid. A combination of this type would be e.g. that with oxacillin or dicloxacillin.

For the purpose of widening the spectrum of action and in order to achieve an increase in action, the compounds according to the invention can also be combined with other antibiotics.

Appendix to the experimental section
List of the eluent mixtures used for chromatography:

I Dichloromethane: methanol
II Toluene: ethyl acetate
III Acetonitrile: water
IV Ethyl acetate
V Petroleum ether: ethyl acetate
VI Dichloromethane: ethanol
VII Toluene: ethanol
VIII Toluene:acetone Abbreviations:
Z Benzyloxycarbonyl
Boc tert-Butyloxycarbonyl
DMF Dimethylformamide
Ph Phenyl
Me Methyl
THF Tetrahydrofuran
CDI Carbonyldiimidazole
DCE Dichloroethane Starting compounds

EXAMPLE I

5-Benzyloxycarbonylamino-benzo[b]thiophene

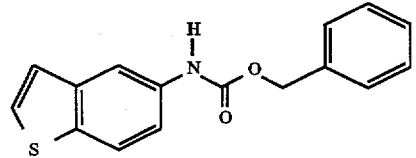

44 ml (294 mmol) of benzyl chloroformate are slowly added dropwise to a solution of 40 g (268 mmol) of 5-amino-benzo[b]thiophene (Synthetic Communications, pp. 959–964 (1991)) in 410 ml of THF, 530 ml of water and 530 ml of satd. NaHCO$_3$ solution. The mixture is allowed to come to RT overnight with stirring the THF is evaporated in vacuo, and the aqueous phase is extracted 3 times with CH$_2$Cl$_2$, dried with Na$_2$SO$_4$ and concentrated. The residue is taken up in a little CH$_2$Cl$_2$, and the solution is diluted with ether (about 200 ml) and mixed slowly with stirring with 1 l of low-boiling petroleum ether. The precipitated solid is filtered off with suction and dried at 50° C. overnight.

Yield: 58.10 g (76.5%)

M.p.: 110° C.

$^1$H-NMR (D$_6$-DMSO, TMS): 9.88 (s, 1H); 8.09 (d, J=1 Hz, 1H); 7.9 (d, J=9 Hz, 1H); 7.73 (d, J=6 Hz, 1H); 7.3–7.5 (m, 7H); 5.2 (s,2H).

The compounds shown in Table I are prepared in analogy to the procedure of Example I:

TABLE I

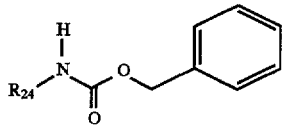

| Ex. No. | R²⁴ | Yield (%) | Mp.: (°C.) | $R_f$ Eluent mixture (ratio) |
|---|---|---|---|---|
| II | 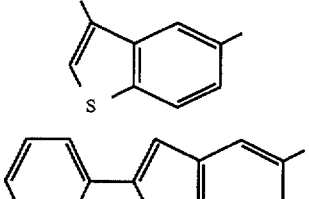 | 98 | 111 | 0.5 (1/1)V |
| III | 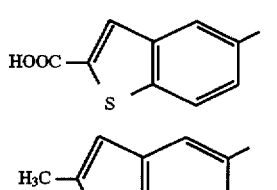 | 55 | — | 0.84 (100/5)I |
| IV | 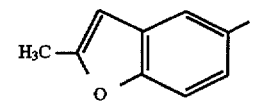 | 98 | 205 with d. | 0.3 (100/5)I |
| V | 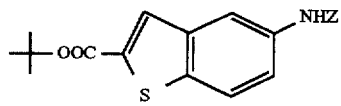 | 82 | 108° C. | 0.68 (5/1)V |

EXAMPLE VI tert-Butyl 5-benzyloxycarbonylamino-benzo[b]thiophene-2-carboxylate

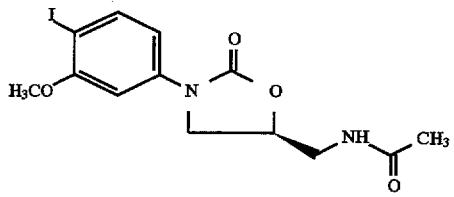

A solution of 25 g (76.4 mmol) of the compound from Example IV, 16.5 g (229 mmol) of t-BuOH and 1.67 g (15.27 mmol) of 4-dimethylaminopyridine in 150 ml of $CH_2Cl_2$ is cooled to −10° C., treated with 16.10 g (84 mmol) of 1-ethyl-3-[3-(dimethylamino)propyl]carbodiimide hydrochloride and brought to RT overnight with stirring. The solution is diluted with 200 ml of $CH_2Cl_2$, washed once each with dilute $H_2SO_4$, satd. $NaHCO_3$ and satd. NaCl solution, dried and concentrated. The crude product thus obtained is chromatographed on silica gel (PE/EA 1:1).

Yield: 7.5 g (26%)

¹H-NMR (D₆-DMSO, TMS): 10.0 (s, 1H); 8.2 (d, J=2 Hz, 1H); 8.06 (s, 1H); 7.93 (d, J=8 Hz, 1H); 7.58 (dd, J=8 Hz, J=2 Hz, 1H); 7.32–7.5 (m, 5H); 5.20 (s, 2H); 1.55 (s, 9H).

EXAMPLE VII (5S)-(3-Methoxy-4-iodophenyl)-5-acetylaminomethyl-2-oxazolidinone 254 mg (1.0 mmol) of iodine in 25 ml of dichloromethane are added to a suspension of 264 mg (1.0 mmol) of (5S)-(3-methoxyphenyl)-5-acetylaminomethyl-2-oxazolidinone (J. Med. Chem. 35 (1992) 1156–1165), 250 mg (1.5 mmol) of silver acetate, 30 ml of dichloromethane and 20 ml of acetonitrile. After 16 h, the mixture is treated with water and dichloromethane, the aqueous phase is extracted with dichloromethane, the combined organic phases are washed with satd. NaCl solution and dried over $MgSO_4$ and the solvents are stripped off in vacuo.

Yield: 370 mg (95%)

¹H-NMR (D₆-CDCl₃, TMS): 7.70 (d, 1H), 7.42 (d, 1H), 6.60 (dd, 1H), 6.25 (bt, 1H), 4.78 (m, 1H), 4.05 (7, 1H), 3.89 (s, 3H), 3.50–3.85 (m, 3H), 2.00 (s, 3H).

EXAMPLE VII (5S)-(3-Hydroxy-4-iodophenyl)-5-acetylaminomethyl-2-oxazolidinone

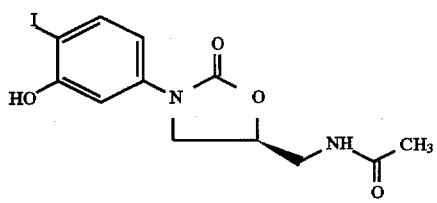

77 ml (77 mmol) of a 1.0M BBr₃ solution in dichloromethane are added dropwise at −78° C. to a solution of 10.0 g (25.6 mmol) of the compound from Example VII in 100 ml of dichloromethane. The mixture is allowed to come to room temperature, and is stirred for a further 3 h, cooled to −10° C. and treated with water. The mixture is treated with ethyl acetate, and the precipitate which is deposited is filtered off with suction and dried.

Yield: 8.0 g (83%)

$R_f$=0.34 (toluene/acetone 1:1)

M.p.: 227°–230° C.

MS (DCI/NH₃): 377 (M⁺+H) $[\alpha]_D^{20}$=−18.76° (DMSO, c=1.0)

¹H-NMR (D₆-DMSO, TMS): 10.5 (bs, 1H), 8.25 (bt, 1H), 7.62 (d, 1H), 7.30 (d, 1H), 6.68 (dd, 1H), 4.70 (m, 1H), 4.05 (t, 1H), 3.70 (dd, 1H), 3.40 (t, 1H), 1.8 (s, 3H).

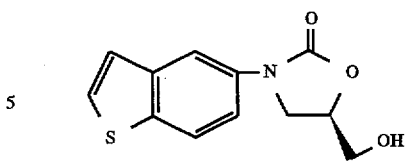

56.55 g (200 mmol) of the compound from Example I are dissolved in 600 ml of THF, treated with 10 mg of 1,10-phenanthroline hydrate and cooled to −70° C. About 80 ml of 2.5N n-butyllithium solution in hexane are then slowly added dropwise until the colour changes to red. 28 ml (200 mmol) of (R)-glycidyl butyrate are then added dropwise. The mixture is allowed to come to RT, treated with saturated ammonium chloride solution, the organic phase is separated off and the aqueous phase is extracted twice with ethyl acetate. The combined organic phases are dried (Na₂SO₄) and concentrated. The residue is stirred in 1 l of ether, filtered off with suction and dried.

Yield: 43.4 g (87.05%)

M.p.: 141° C. $[\alpha]_D^{20}$=−58.9° (DMSO, c=1.0)

MS (EI): 249 (M⁺, 100%)

¹H-NMR (D₆-DMSO, TMS): 7.95–8.07 (m, 2H); 7.8 (d, J=5 Hz, 1H); 7.7 (dd, J=10 Hz, J=2 Hz, 1H); 7.45 (d, J=5 Hz, 1H); 5.23 (t, J=6 Hz, 1H); 4.67–4.8 (m, 1H); 4.15 (t, J=9 Hz, 1H); 3.92 (dd, J=9 Hz, J=5 Hz, 1H); 3.52–3.78 (m, 2H).

TABLE 1

| Ex. No. | R²⁴ | Prepared from Ex. No. | Yield (% of theory) | M.p.: (°C.) | R_f eluent mixture (ratio) |
|---|---|---|---|---|---|
| 2 | (3-methylbenzo[b]thiophen-2-yl) | II | 91 | 126 | 0.25 (3/7)V |
| 3 | (3-phenylbenzo[b]thiophen-2-yl) | III | 95 | 218 with d. | 0.5 (100/5)I |
| 4 | (3-tert-butoxycarbonylbenzo[b]thiophen-2-yl) | IV | 73 | 130 | 0.1 (1/1)V |
| 5 | (3-methylbenzofuran-2-yl) | V | 78 | 166 | 0.19 (1/1)V |

PREPARATION EXAMPLES

EXAMPLE 1

(5R)-3-[5-Benzo[b]-thiophenyl]-5-hydroxymethyl-oxazolidine-2-one

EXAMPLE 6

(5R)-3-[5-Benzo[b]-thiophenyl]-5-methanesulphonylmethyl-oxazolidine-2-one

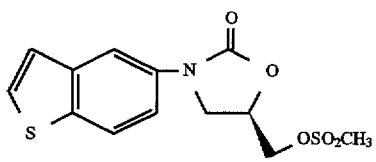

A solution of 42.4 g (170 mmol) of the compound from Example 1 and 59 ml (425 mmol) of triethylamine in 2 l of THF is cooled to −10° C. and slowly treated with 29 ml (374 mmol) of methanesulphonyl chloride. The mixture is stirred at −10° C. for 2 h, solid is filtered off with suction and the residue is washed 3 to 4 times with $CH_2Cl_2$. After the solvent mixture has been stripped off on a rotary evaporator, the residue is dissolved in $CH_2Cl_2$ and washed once each with satd. $NaHCO_3$, dil. $H_2SO_4$ and dil. NaCl solution. After drying ($Na_2SO_4$) and concentrating the product is obtained sufficiently pure for further reactions.

Yield: 55.6 g (100%)

EXAMPLE 7

(5R)-3-[5-Benzo[b]thiophenyl]-5-azidomethyl-oxazolidin-2-one

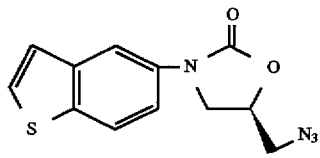

55 g (168 mmol) of the compound from Example 6 are dissolved in 390 ml of DMF and treated with 12 g (185 mmol) of sodium azide. The reaction mixture thus obtained is stirred at 70° C. for 14 h. It is allowed to cool to RT and is poured into 3 l of ice-water. The precipitated solid is filtered off with suction, washed with water and petroleum ether and dried in air.

Yield: 43 g (93%)

M.p.: 108° C. $[\alpha]_D^{20}$=−144.7° (DMSO, c=1.0)

MS: 275 ($M^+$+1, 100%)

$^1$H-NMR ($D_6$-DMSO, TMS): 7.98–8.08 (m, 2H); 7.8 (d, J=5 Hz, 1H); 7.68 (dd, J=10 Hz, J=2 Hz, 1H); 7.45 (d, J=5 Hz, 1H); 4.85–5.0 (m, 1H); 4.21 (t, J=9 Hz, 1H); 3.86 (dd, J=9 Hz, J=5 Hz, 1H); 3.75 (t, J=6 Hz, 2H).

EXAMPLE 8

(5R)-3-[5-Benzo[b]-thiophenyl]-5-aminomethyl-oxazolidin-2-one hydrochloride

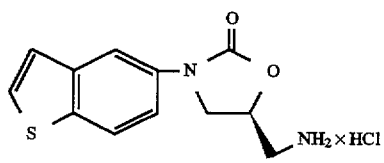

43 g (157 mmol) of the compound from Example 7 are dissolved in 110 ml of ethylene glycol dimethyl ether and the solution is heated to 50° C. 22.2 ml (188 mmol) of trimethyl phosphite are slowly added dropwise (evolution of gas), and the mixture is heated to 90° C. after addition is complete and stirred at 90° C. for 5 h. 30 ml (180 mmol) of 6N HCl are then added dropwise and the mixture is again stirred at 90° C. for 5 h. It is allowed to cool to RT, and the precipitate which is deposited is filtered off with suction, stirred in 1 l of ether for 1 h, filtered off with suction again and dried at 50° C.

Yield: 44 g (98%)

M.p.: 195° C.

MS (DCI): 249 ($M^+$+1, 100%)

EXAMPLE 9

(5S)-3-[5-Benzo[b]thiophenyl]5-acetylamino-methyl-oxazolidin-2-one

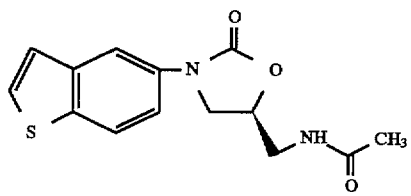

43 g (151 mmol) of the compound from Example 8 are treated with 320 ml of $CH_2Cl_2$ and 54 ml (407 mmol) of triethylamine. The reaction solution thus obtained is cooled to 0° C. with stirring and slowly treated with 16.5 ml (233 mmol) of acetyl chloride. The mixture is subsequently stirred at 0° C. for 5 h and is diluted with 400 ml of water and 300 ml of $CH_2Cl_1$. The organic phase is separated off and washed once each with dilute $H_2SO_4$, satd. $NaHCO_3$ and satd. NaCl solution. After drying ($Na_2SO_4$) and concentrating, contaminated product is obtained which is chromatographed on silica gel (methylene chloride:methanol 100:2).

Yield: 32.5 g (74.2%)

$R_f$=0.26 ($CH_2Cl_2$/$CH_3OH$=100/5)

M.p.: 160° C.

$^1$H-NMR ($D_6$-DMSO): 8.28 (t, J=7 Hz, 1H); 7.95–8.05 (m, 2H); 7.8 (d, J=5Hz, 1H);7.69 (dd, J=10 Hz, J=2 Hz, 1H); 7.45 (d, J=5 Hz, 1H); 4.7–4.83(m, 1H): 4.2 (t, J=9 Hz, 1H); 3.85 (dd, J=9 Hz, J=5 Hz, 1H); 3.45 (t, J=6 Hz, 2H); 1.85 (s, 3H).

The compounds shown in Table 2 are prepared in analogy to the procedures of Examples 5 to 9:

TABLE 2

| Ex. No. | R²⁴ | R⁶ | Yield (% of theory) | M.p.: (°C.) | Prepared from Ex. No. | R_f Eluent mixture (ratio) |
|---|---|---|---|---|---|---|
| 10 | 3-methyl-benzo[b]thiophen-2-yl | acetyl | 78 | 163 | 2 | |
| 11 | 3-carboxy-benzo[b]thiophen-2-yl | acetyl | 51 | | 4 | |
| 12 | 3-phenyl-benzo[b]thiophen-2-yl | acetyl | 14 | 244 | 3 | |
| 13 | 3-phenyl-benzo[b]thiophen-2-yl | propionyl | 22 | 251 | 3 | |
| 14 | 3-phenyl-benzo[b]thiophen-2-yl | methoxycarbonyl | 28 | 193 | 3 | |
| 15 | 3-phenyl-benzo[b]thiophen-2-yl | cyclopropylcarbonyl | 29 | 255 | 3 | |
| 16 | 2-methyl-benzofuran-3-yl | acetyl | 83 | 135 | 5 | 0.43 (10/1)VI |

EXAMPLE 17

(5S)-3-[5-(2-Bromo-benzo[b]thiophenyl)]-5-acetylamino-methyl-oxazolidin-2-one

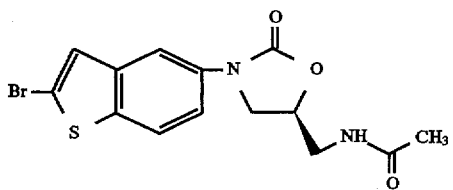

5 g (17.2 mmol) of the compound from Example 9 are dissolved in 55 ml of chloroform and 35 ml of acetonitrile and cooled to 0° C. A solution of 0.88 ml (17.2 mmol) of bromine in 10 ml of chloroform is then slowly added dropwise and the mixture is stirred at RT for 72 h. The precipitate which is deposited is filtered off with suction and stirred for 16 h with 100 ml of sad. NaHCO₃ solution. The precipitate is filtered off with suction, washed well with water and ether and dried at 50° C.

Yield: 4.01 g (63%)

M.p.: 132° C.

$^1$H NMR ($D_6$-DMSO): 8.28 (t, J=7 Hz, 1H); 8.1 (d, J=10 Hz, 1H); 8.07 (s, 1H); 7.92 (d, J=2 Hz, 1H); 7.7 (dd, J=10 Hz, J=2 Hz, 1H); 4.72–4.82 (m, 1H); 4.26 (t, J=9 Hz, 1H); 3.90 (dd, J=9 Hz, J=5 Hz, 1H); 3.47 (t, J=6 Hz, 2H); 1.83 (s, 3H).

The compounds shown in Table 3 are prepared in analogy to the procedure of Example 17:

TABLE 3

| Ex. No. | R[24] | Yield (% of theory) | M.p.: (°C.) | Prepared from Ex. No. | R_f Eluent mixture (ratio) |
|---|---|---|---|---|---|
| 18 | (3-methyl-5-methylbenzo[b]thiophen-2-yl, Br) | 88 | 103 | 10 | 0.26 (100/5)I |
| 19 | (2-methyl-5-methylbenzofuran-3-yl, Br) | 57 | 171 | 16 | 0.63 (1/1)VII |

EXAMPLE 20

(5S)-3-[5-(2-Phenyl-3-methyl-benzo[b]thiophenyl)]-5-acetylaminomethyloxazolidin-2-one

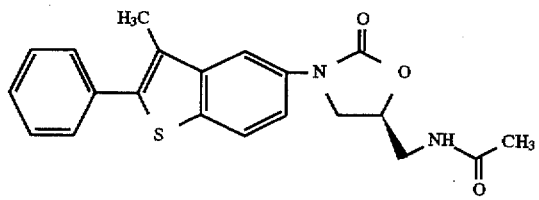

383 mg (1 mmol) of the compound from Example 18 and 159 mg (1.3 mmol) of phenylboronic acid are dissolved in 8 ml of THF, treated with 34 mg (0.029 mmol) of Pd(P(C$_6$H$_5$)$_3$)$_4$ and the solution is boiled under reflux for 1 h. 1.4 ml of 2M Na$_2$CO$_3$ solution are added and the mixture is boiled under reflux for 16 h, cooled to RT and concentrated and the residue is chromatographed on silica gel (CH$_2$Cl$_2$/CH$_3$OH 100:1).

Yield: 336 mg (88%)

M.p.: 205° C.

R$_f$=0.22 (CH$_2$Cl$_2$/CH$_3$OH 100/5)

MS: 380 (M$^+$, 100%)

$^1$H-NMR (D$_6$-DMSO, TMS): 8.28 (t, J=7 Hz, 1H); 7.98 (d, J=10 Hz, 1H); 7.88 (d, J=2 Hz, 1H); 7.7 (dd, J=2 Hz, J=10 Hz, 1H); 7.4–7.62 (m, 5H); 4.7–4.85 (m, 1H); 4.28 (t, J=9 Hz, 1H); 3.89 (dd, J=9 Hz, J=5 Hz, 1H); 3.45 (t, J=6 Hz, 2H); 2.42 (s, 3H); 1.85 (s, 3H).

The compounds shown in Table 4 are prepared in analogy to the procedure of Example 20:

TABLE 4

| Ex. No. | R[24] | Yield (% of theory) | M.P: (°C.) | Prepared from Ex. No. | R_f Eluent mixture (ratio) |
|---|---|---|---|---|---|
| 21 | (2-(4-formylphenyl)-3-methyl-5-methylbenzo[b]thiophen-2-yl) | 90 | 191 | 18 | 0.28 (100/5)I |

TABLE 4-continued

[structure: R²⁴—N-oxazolidinone with CH₂-NH-C(O)-CH₃ substituent]

| Ex. No. | R²⁴ | Yield (% of theory) | M.P: (°C.) | Prepared from Ex. No. | R_f Eluent mixture (ratio) |
|---|---|---|---|---|---|
| 22 | OHC-phenyl-CH=C(benzothiophene-methyl) | 89 | 122 | 17 | 0.24 (100/5)I |
| 23 | CH₃C(O)-phenyl-CH=C(benzothiophene-methyl) | 83 | 215 with d. | 17 | 0.24 (100/5)I |
| 24 | F-phenyl-CH=C(benzothiophene-methyl) | 86 | 187 | 17 | 0.44 (100/5)I |
| 25 | pyridyl-C=C(benzothiophene-methyl) × HCl | 59 | 167 n.Z. | 17 | 0.14 (100/5)I |

EXAMPLE 26

(5S)-3-{5-[(2-Bromo-1,1-dioxo-3-methyl)benzo[b]thiophenyl]}-5-acetylaminomethyloxazolidine-2-one

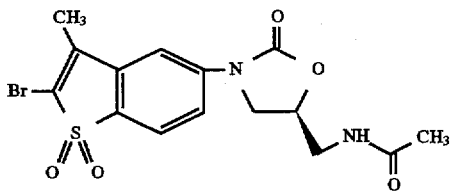

192 mg (0.5 mmol) of the compound from Example 18 and 344 mg (1.2 mmol) of meta-chloroperbenzoic acid are dissolved in 2.5 ml of CH₂Cl₂ and the mixture is stirred at RT for 48 h. The batch is diluted with 20 ml of ether and 10 ml of satd. NaHCO₃ solution and the mixture is stirred at RT for 1 h. The precipitate which is deposited is filtered off with suction, washed with ether and dried at 50° C.

Yield: 146 mg (71%)

$R_f$=0.17 (CH₂Cl₂/CH₃OH 100/3)

M.P.: 243° C.

MS (FAB): 415 (M⁺, 100%)

¹H-NMR (D₆-DMSO, TMS): 8.25 (t, J=7 Hz, 1H); 8.0 (d, J=10 Hz, 1H); 7.85 (d, J=2 Hz, 1H); 7.73 (dd, J=10 Hz, J=2 Hz, 1H); 4.75–4.88 (m, 1H); 4.23 (t, J=9 Hz, 1H); 3.84 (dd, J=9 Hz, J=5 Hz, 1H); 3.46 (t, J=6 Hz, 2H); 2.28 (s, 3H); 1.83 (s, 3H).

The compounds shown in Table 5 are prepared in analogy to the procedure of Example 26:

TABLE 5

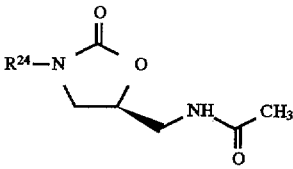

| Ex. No. | R24 | Yield (% of theory) | M.P: (°C.) | Prepared from Ex. No. | Rf Eluent mixture (ratio) |
|---|---|---|---|---|---|
| 27 | (5-methyl-benzo[b]thiophene 1,1-dioxide) | 66 | 202 with d. | 9 | |

EXAMPLE 28

(5S)-(2-Hydroxymethyl-benzofuran-6-yl)-5-acetylaminomethyl-2-oxazolidinone

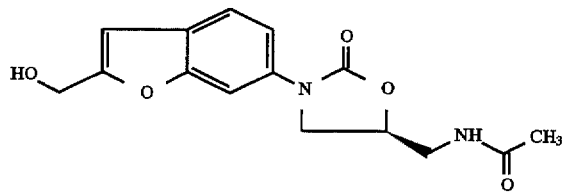

A mixture of 100 mg (0.27 mmol) of the compound from Example VIII, 55 mg (0.66 mmol) of sodium acetate, 30 mg (0.54 mmol) of propargyl alcohol, 40 mg (0.05 mmol) of bis(triphenylphosphino)palladium(II) acetate and 20 mg (0.1 mmol) of copper iodide in 2 ml of DMF is stirred at 60° C. for 14 h. The batch is added to ice-water and extracted with ethyl acetate, the combined organic phases are dried over $Na_2SO_4$, the solvents are stripped off in vacuo and the residue is purified by chromatography (toluene/acetone) and recrystallization.

Yield: 40 mg (58%)

$R_f$=0.25 (toluene/acetone 1/1)

M.P.: 142°–144° C.

MS (EI): 304 (M$^+$)

$^1$H-NMR (D$_6$-DMSO, TMS): 8.25 (bt, 1H), 7.75 (s, 1H), 7.57 (d, 1H), 7.40 (dd, 1H), 6.70 (s, 1H), 5.45 (t, 1H), 4.70 (m, 1H), 4.55 (d, 2H), 4.20 (t, 1H), 3.75 (dd, 1H), 3.45 (m, 2H), 1.85 (s, 3H).

The compounds shown in Table 6 are prepared in analogy to the procedure of Example 28:

TABLE 6

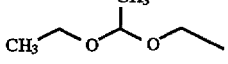

| Ex. No. | D | Yield (% of theory) | Rf (Eluent mixture) ratio | MS (DCI, M+ + H) |
|---|---|---|---|---|
| 29 | (CH3-CH(O-CH2CH3)-O-) structure | 71 | 0.38 (VIII) 1:1 | 376 |
| 30 | (HO-CH2CH2-N(C6H5)-CH2CH3) structure | 28 | 0.38 (VIII) 1:1 | 424 |
| 34 | (H3C-C(O)-NH-C6H4-O-CH2CH3) structure | 36 | 0.19 (VII) 1:1 | 438 |

We claim:

1. An oxazolidinone of the formula

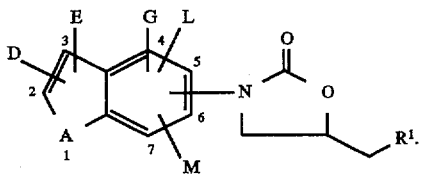

in which

R¹ represents azido, hydroxyl or a group of the formula —OR², —O—SO₂R³ or —NR⁴R⁵, wherein R² denotes a straight-chain or branched acyl having up to 6 carbon atoms or benzyl, R³ denotes straight-chain or branched alkyl having up to 4 carbon atoms or phenyl which is optionally substituted by straight-chain or branched alkyl having up to 4 carbon atoms, R⁴ and R⁵ are identical or different and denote cycloalkyl having 3 to 6 carbon atoms, hydrogen, phenyl, straight-chain or branched alkyl or alkoxy having up to 8 carbon atoms, tert-butoxycarbonyl or benzyloxycarbonyl, or R⁴ and R⁵ denotes a group of the formula —CO—R⁶, wherein R⁶ denotes cyclopropyl, cyclobutyl, cyclopentyl, cyclohexyl or straight-chain or branched alkyl or alkoxy in each case having up to 6 carbon atoms, hydrogen or phenyl, A represents an oxygen or sulphur atom, D, E, G, L and M are identical or different and represent hydrogen, carboxyl, fluorine, chlorine, bromine, cyano, formyl, trifluoromethyl, straight-chain or branched alkoxy, alkoxycarbonyl or acyl in each case having up to 6 carbon atoms or straight-chain or branched alkyl having up to 6 carbon atoms, which for its parts is optionally substituted by hydroxy, by straight-chain or branched alkoxy or acyl having up to 5 carbon atoms, by a radical of the formula

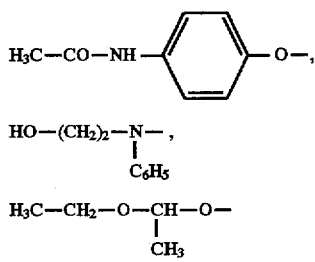

or by a group of the formula —NR⁷R⁸, wherein

R⁷ and R⁸ are identical or different and denote hydrogen, straight-chain or branched alkyl having up to 3 carbon atoms or phenyl, and/or D, E, G, L and/or M optionally represent a group of the formula —NR⁷'R⁸', wherein R⁷' and R⁸' have the meaning of R⁷ and R⁸ indicated above and are identical to or different from this and/or one of D, E, G, L and M optionally represents iodine and/or one of D, E, G, L and M optionally represents nitro, and/or D, E, G, L or M optionally represent (C₂-C₄)-alkenylphenyl, phenyl, pyridyl or thienyl which for their parts are optionally substituted by a group of the formula —CO—NR⁹R¹⁰, —N¹¹R¹², wherein R⁹ and R¹⁰ are identical or different and denote hydrogen straight-chain or branched alkyl having up to 4 carbon atoms or phenyl, R¹¹ and R¹² are identical or different and have the meaning of R⁷ and R⁸ indicated above and are identical or different from them, which said (C₂-C₄)-alkenylphenyl, phenyl, pyridyl or thienyl for their parts are optionally substituted up to 2 times by identical or different substituents from the group consisting of carboxyl, fluorine, chlorine, bromine, iodine, cyano, mercapto, formyl, trifluoromethyl, nitro, phenyl, or straight-chain or branched alkoxy, alkoxycarbonyl, alkylthio and acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms or by a group of the formula —NR¹⁸R¹⁹, wherein R¹⁸ and R¹⁹ have the meaning of R⁷ and R⁸ indicated above and are identical to or different from this, or a salt or S-oxide thereof.

2. An oxazolidinone according to claim 1, wherein

R¹ represents azido, hydroxyl or a group of the formula —OR², —OSO₂R³ or —NR⁴R⁵, wherein R² denotes straight-chain or branched acyl having up to 6 carbon atoms or benzyl, R³ denotes methyl ethyl, phenyl or toluoyl, R⁴ and R⁵ are identical or different and denote cyclopropyl, cyclopentyl, cyclohexyl, hydrogen, phenyl or straight-chain or branched alkyl or alkoxy in each case having up to 5 carbon atoms, tert-butoxycarbonyl or benzyloxycarbonyl, or R⁴ or R⁵ denotes a group of the formula —CO—R⁶, wherein R⁶ denotes cyclopropyl, cyclobutyl, cyclopentyl, cyclohexyl or straight-chain or branched alkyl or alkoxy in each case having up to 4 carbon atoms, phenyl or hydrogen, A represents an oxygen or sulphur atom, D, E, G, L and M are identical or different and represent hydrogen, carboxyl, fluorine, chlorine, bromine, cyano, mercapto, trifluoromethyl, formyl, straight-chain or branched alkoxy, alkoxycarbonyl or acylthio or acyl in each case having up to 4 carbon atoms or straight-chain or branched alkyl having up to 4 carbon atoms, which for its parts is optionally substituted by hydroxy, by straight-chain or branched alkoxy or acyl having up to 4 carbon atoms, by a radical of the formula

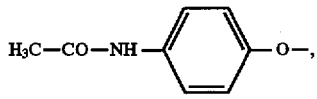

-continued

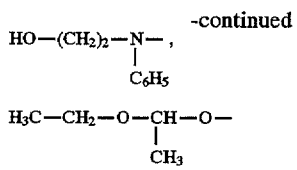

or by a group of the formula —NR$^7$R$^8$,
wherein
R$^7$ and R$^8$ are identical or different and denote hydrogen, or methyl,
and/or D, E, G, L and/or M
optionally represent a group of the formula —NR$^{7'}$R$^{8'}$,
wherein
R$^{7'}$ and R$^{8'}$ have the meaning of R$^7$ and R$^8$ indicated above and are identical to or different from this,
and/or D, E, G, L and M
optionally represent iodine and one of D, E, G, L or M optionally represents nitro,
and/or D, E, G, L and/or M
optionally represent 2-phenylvinyl or phenyl which for their parts are optionally substituted
by a group of the formula —CO—NR$^9$R$^{10}$, —N$^{11}$R$^{12}$,
wherein
R$^9$ and R$^{10}$ are identical or different and denote hydrogen or methyl,
R$^{11}$ and R$^{12}$ are identical or different and have the meaning of R$^7$ and R$^8$ indicated above and are identical to or different from this, which said for their parts are optionally substituted up to 2 times by identical or different substituents from the group consisting of carboxyl, fluorine, chlorine, bromine, iodine, cyano, mercapto, trifluoromethyl, formyl, nitro, phenyl, straight-chain or branched alkoxy, alkoxycarbonyl, alkylthio and acyl in each case having up to 4 carbon atoms or straight-chain or branched alkyl having up to 4 carbon atoms, which for its part can optionally be substituted by hydroxyl, by straight-chain or branched alkoxy or acyl having up to 4 carbon atoms or by a group of the formula —NR$^{18}$R$^{19}$,
wherein
R$^{18}$ and R$^{19}$ have the meaning of R$^7$ and R$^8$ indicated above and are identical to or different from this,
or a salt or S-oxide thereof.

3. An oxazolidinone according to claim 1, in which G, L and M represent hydrogen and the oxazolidinone radical is bonded to the phenyl ring in position 5 to 6.

4. An oxazolidinone according to claim 1, of the formula

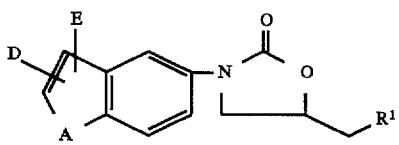

in which
R$^1$ represents N$_3$, OH, —OSO$_2$R$^3$ or —NR$^4$R$^5$
wherein
R$^3$ represents straight-chain or branched alkyl having up to 4 carbon atoms or phenyl which is optionally substituted by a straight-chain or branched alkyl having up to 4 carbon atoms,
R$^4$ and R$^5$ are identical or different and represent hydrogen, straight-chain or branched alkyl having up to 8 carbon atoms, cycloalkyl having 3 to 6 carbon atoms, or phenyl, or
R$^4$ and R$^5$ denotes a group of the formula —CO—R$^6$,
wherein
R$^6$ denotes cycloalkyl having 3 to 6 carbon atoms, straight-chain or branched alkyl or alkoxy in each case having up to 4 carbon atoms, phenyl or hydrogen,
A represents an oxygen or sulphur atom,
D and E independently represent hydrogen, carboxyl, fluorine, chlorine, bromine, iodine cyano, mercapto, formyl, trifluoromethyl nitro, straight-chain or branched alkoxy, alkoxycarbonyl, alkylthio or acyl in each case having up to 6 carbon atoms, or straight-chain or branched alkyl having up to 6 carbon atoms, which for its parts can be substituted by hydroxyl, by straight-chain or branched alkoxy or acyl having up to 5 carbon atoms or by a radical of the formula

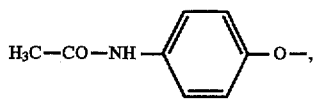

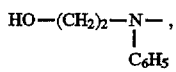

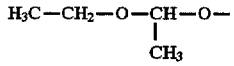

and/or one of D or E optionally represents iodine and/or one of E or E represents iodine.

5. An oxazolidinone according to claim 4, wherein
R$^1$ represents N$_3$, OH, —OSO$_2$R$^3$ or —NR$^4$R$^5$
wherein
R$^3$ represents straight-chain or branched alkyl having up to 4 carbon atoms or phenyl which is optionally substituted by a straight-chain or branched alkyl having up to 4 carbon atoms,
R$^4$ and R$^5$ are identical or different and represent hydrogen, straight-chain or branched alkyl having up to 6 carbon atoms, cycloalkyl having 3 to 6 carbon atoms, or phenyl, or
R$^4$ and R$^5$ denotes a group of the formula —CO—R$^6$,
D independently represent hydrogen, carboxyl, fluorine, chlorine, bromine, iodine, cyano, mercapto, formyl, trifluoromethyl, nitro, straight-chain or branched alkoxy, alkoxycarbonyl, alkylthio or acyl in each case having up to 6 carbon atoms, or straight-chain or branched alkyl having up to 6 carbon atoms, which for its parts can be substituted by hydroxyl, by straight-chain or branched alkoxy or acyl having up to 5 carbon atoms or by a radical of the formula

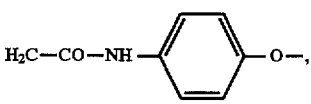

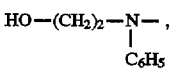

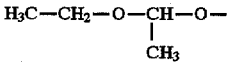

E represents hydrogen or methyl.

6. An oxazolidinone according to claim 4, wherein D represents hydrogen.

7. An oxazolidinone according to claim 4, wherein

R¹ represents —NR⁴R⁵, and

R⁴ and R⁵ denotes a group of the formula —CO—R⁶,

R⁶ denotes cyclopropyl, cyclopentyl, cyclohexyl or straight-chain or branched alkyl or alkoxy in each case having up to 4 carbon atoms, hydrogen or phenyl.

8. A compound according to claim 1, wherein such compound is

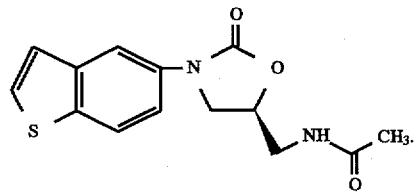

9. A compound according to claim 1 wherein such compound is

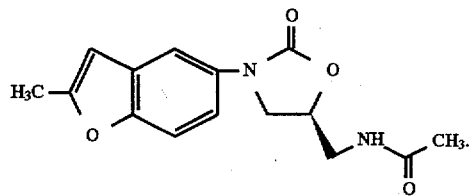

10. A pharmaceutical composition which comprises an effective amount of a compound or a pharmaceutically acceptable salt or S-oxide thereof according to claim 1 and a inert carrier.

11. A method for treating bacterial infections in a host in need thereof which comprises administering to said host an effective amount of a compound or a pharmaceutically acceptable salt or S-oxide thereof according to claim 1.

* * * * *